(12) United States Patent
Le Huec

(10) Patent No.: US 8,163,020 B2
(45) Date of Patent: Apr. 24, 2012

(54) ASSEMBLY COMPRISING AN IMPLANT FOR REPLACING A VERTEBRAL BODY AND A SPINAL DISTRACTION TOOL

(75) Inventor: Jean-Charles Le Huec, Pessac (FR)

(73) Assignee: Creaspine (FR)

( * ) Notice: Subject to any disclaimer, the term of this patent is extended or adjusted under 35 U.S.C. 154(b) by 876 days.

(21) Appl. No.: 12/158,811

(22) PCT Filed: Dec. 20, 2006

(86) PCT No.: PCT/FR2006/051401
§ 371 (c)(1),
(2), (4) Date: Jun. 23, 2008

(87) PCT Pub. No.: WO2007/074295
PCT Pub. Date: Jul. 5, 2007

(65) Prior Publication Data
US 2009/0048673 A1    Feb. 19, 2009

(30) Foreign Application Priority Data
Dec. 22, 2005 (FR) ..................................... 05 13152

(51) Int. Cl.
*A61F 2/44* (2006.01)
(52) U.S. Cl. .................................................. 623/17.11

(58) Field of Classification Search ................. 606/86 A, 606/90; 623/17.11–17.16
See application file for complete search history.

(56) References Cited

U.S. PATENT DOCUMENTS

| 4,747,394 A | 5/1988 | Watanabe et al. | |
| 2001/0005796 A1* | 6/2001 | Zdeblick et al. | 623/17.11 |
| 2004/0122518 A1 | 6/2004 | Rhoda | |
| 2006/0200244 A1* | 9/2006 | Assaker | 623/17.15 |

FOREIGN PATENT DOCUMENTS

| WO | 0045751 | 8/2000 |
| WO | 02071986 | 9/2002 |

OTHER PUBLICATIONS

International Search Report PCT/FR2006/051401 Dated Jun. 11, 2007.

* cited by examiner

*Primary Examiner* — Eduardo C Robert
*Assistant Examiner* — Summer Kostelnik
(74) *Attorney, Agent, or Firm* — Cantor Colburn LLP

(57) ABSTRACT

The invention relates to an assembly comprising: an implant (18b), the two ends of which are equipped with plates (19, 20) which are provided with slots (28); and a distraction tool consisting of blades (2) which are intended to co-operate with the slots (28). The widths of the slots (28) correspond to those of the blades (2), but the depth of the slots (28) is greater than that of the blades (2).

14 Claims, 7 Drawing Sheets

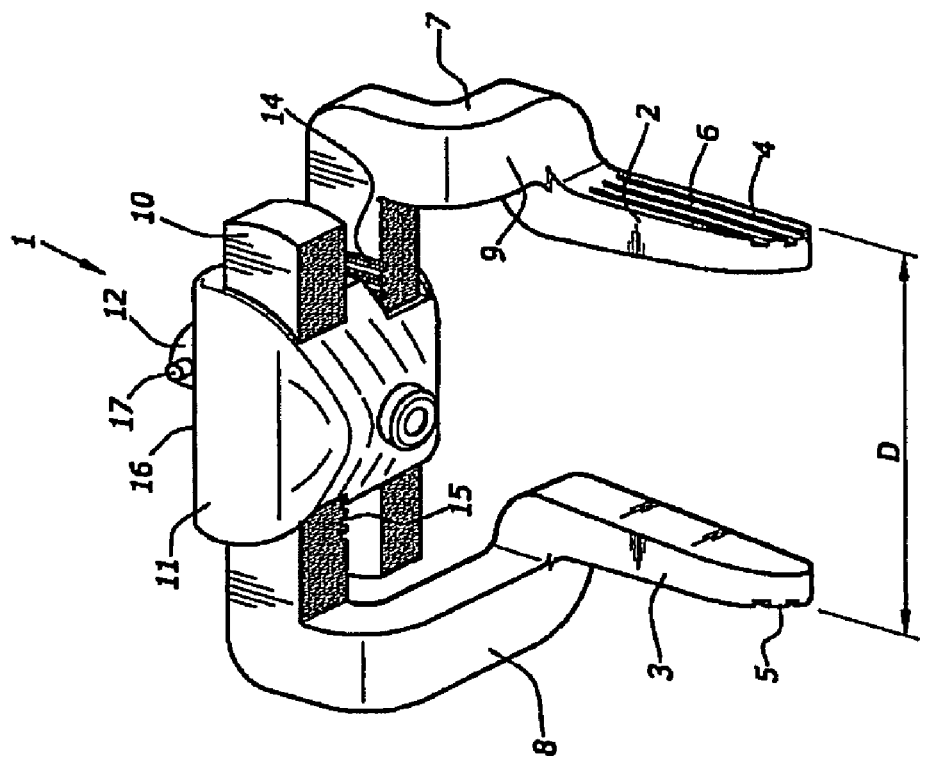
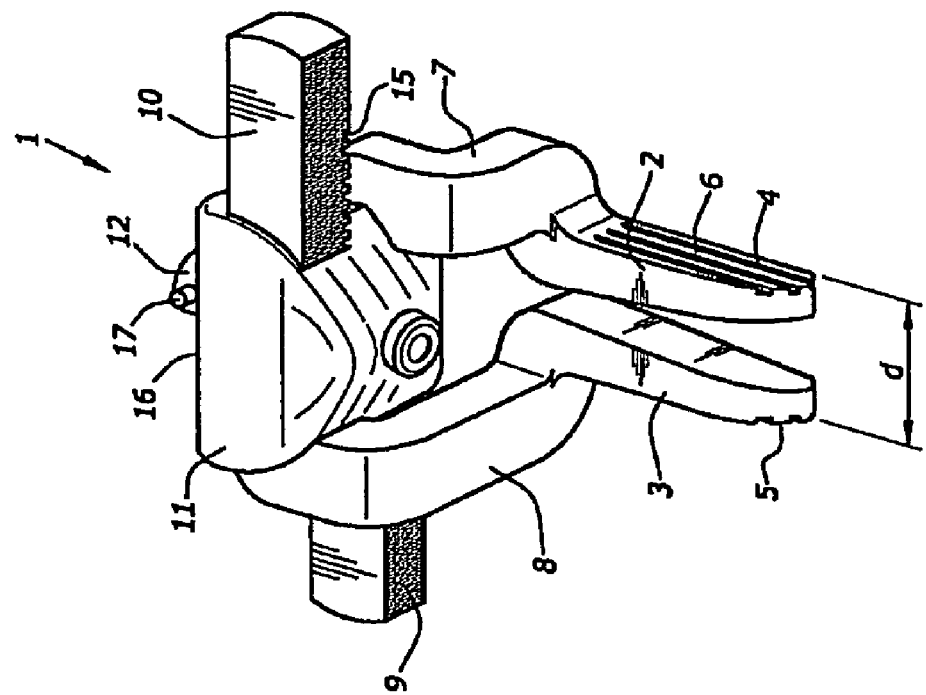

ASSEMBLY COMPRISING AN IMPLANT FOR REPLACING A VERTEBRAL BODY AND A SPINAL DISTRACTION TOOL

TECHNICAL FIELD OF THE INVENTION

The invention relates to the field of surgery of the vertebral column and, more particularly, to surgery following damage such as a fracture or the appearance of a tumor that has required at least partial ablation of a vertebral body.

BRIEF DISCUSSION OF RELATED ART

When fitting implants intended to replace a vertebral body whose at least partial ablation has been required, especially in the thoracolumbar region, it is first necessary to restore the natural lordosis before inserting the implant. This can be done by manual posterior pressure opposing the local kyphosis created by the corpectomy. However, this method is dangerous and rather ineffective.

Another technique is to perform a distraction of the vertebrae between which the implant is to be inserted. This can be done by implanting screws in the vertebrae, then spacing said vertebrae apart by means of an instrument bearing on said screws. The screws will then be able to be used for fixation of instrumentation with rod(s) or plate(s) that will stabilize the assembly.

If the screws are posterior pedicle screws, the surgery must comprise both a posterior approach, for the implantation and spacing apart of the screws, and an anterior approach for the placement of the implant. To shorten the duration of the operation and to simplify its implementation, it is therefore preferable to implant the screws in the anterior region.

A drawback of this technique is that the distraction force exerted on the screws risks adversely affecting their anchorage in the bone, and the quality of the fixation of the instrumentation will not be able to be guaranteed. Moreover, since the distraction is performed on just one side, it tends to create local scoliosis. It is not thus possible to obtain a distraction that would keep the vertebral plateaus substantially parallel. Document U.S. Pat. No. 6,648,891, in particular, describes a device with which such distraction can be performed (but it does not envision the use of screws for subsequent fixation of the plate constituting the stabilization device).

There is therefore a need for a vertebral distraction device which, on the one hand, provides a distraction keeping the vertebral plateaus substantially parallel, and which, on the other hand, does not impede but indeed facilitates the insertion of the implant and could be withdrawn without affecting this insertion.

BRIEF SUMMARY OF THE INVENTION

For this purpose, the invention relates to an assembly comprising:
a) an implant intended to replace all or part of a vertebral body of a damaged vertebra, having
 a central part comprising a bone graft and/or a tubular cage with a solid or perforated wall;
 two plates which are arranged at the ends of said central part and whose flat outer faces are intended to come into contact with the vertebral plateaus of the healthy vertebrae enclosing the damaged vertebra and are each provided with a slot, and
b) a spinal distraction device, having:
 two blades which face each other and each have a flat outer face intended to come into contact with a vertebral plateau of a healthy vertebra, said blades each being connected to a rack;
 a central part traversed by said racks and enclosing a pinion whose teeth are in contact with said racks in such a way that a rotation of said pinion causes said blades to move toward or away from each other, and
 means for controlling said pinion in rotation,
this assembly being characterized in that said slots are each designed to receive said blades, the width of these slots corresponding to the widths of these blades, but the depth of these slots being greater than or equal to the thickness of said blades.

According to other optional features of this assembly:
 said blades are each connected to said racks via a sinuous portion, these sinuous portions being configured in such a way as to form an offset between said blades and said central part in order to permit free access to the space posterior to said blades,
 the outer faces of the blades are parallel,
 the outer faces of said plates are parallel,
 the outer faces of said blades form an angle corresponding to an angle of lordosis or kyphosis of the spine,
 the outer faces of said plates form an angle corresponding to a lordosis or kyphosis of the spine,
 said plates have apertures,
 said central part and said plates form a single piece,
 said plates are attached and fixed to said central part,
 said plates have threaded holes for engagement of screws ensuring their connection to said central part,
 said control means comprise a tool that is able to cooperate with said pinion in a movable manner,
 this assembly comprises a pin passing through said pinion and permitting engagement of this pinion with said tool,
 this assembly comprises surfaces formed at one end of said pinion and permitting engagement of this pinion with said tool.

The present invention also relates to a device for assembling an implant that forms part of an assembly according to the above, characterized in that it comprises a base provided with a seat, of which one end is a fixed wall which on its face directed toward the seat has a horizontal crosspiece with a width corresponding to that of a slot of the implant, and of which the other end is a rod movable in the longitudinal axis of the seat and having, on its face directed toward the seat, a crosspiece with a width corresponding to that of a slot of the implant, said crosspieces facing each other.

The present invention also relates to a tool forming part of an assembly according to the above, characterized in that it comprises a rod provided at one of its ends with a handle and at the other end with a bushing whose internal space is designed to engage, without possible rotation, with the posterior face of the central part of the distraction device, said rod enclosing an inner rod which can be controlled so as to turn about its longitudinal axis and can be blocked in rotation and, at its end, has means for engaging it with the pinion.

As will have been understood, the invention is based principally on the use of two devices:
 a distractor comprising two substantially parallel blades which are placed opposite each other and whose flat outer faces are intended to bear against the vertebral plateaus after the corpectomy; a rack system that can be actuated by a suitable tool, connects these two blades and allows them to be spaced apart under the control of the surgeon, while being kept parallel;

and an implant whose general shape can be cylindrical and is intended to replace a vertebral body that has been at least partially removed; this implant comprises two end elements, or plates, which are connected to each other by a bone graft that is fixed to them, either via a tubular part, such as a tube with a solid wall or a tubular lattice made of titanium, that can enclose a bone graft.

The plates comprise slots that permit insertion of the implant between the blades of the distractor when the latter is in place. By means of such insertion, no over-distraction of the vertebral plateaus is necessary. In other words, it is enough to space these vertebral plateaus apart from each other by a distance scarcely any greater than the length of the implant, which minimizes the impact of the operation in the region concerned.

After this insertion, the blades of the distractor are brought together until the vertebral plateaus come into contact with the outer surfaces of the plates of the implant and begin to compress the latter. The distractor is then withdrawn, this last phase being facilitated by the fact that the depth of the slots in the implant is greater than that of the blades of the distractor. By virtue of this feature, the blades of the distractor do not apply any friction to the vertebral plateaus as said blades are being withdrawn.

The invention also relates to an assembling device which is used to assemble the implant before the latter is fitted in place.

BRIEF DESCRIPTION OF THE DRAWINGS

The invention will be better understood on reading the following description given with reference to the attached figures, in which:

FIGS. 1 and 2 show perspective views of an example of a spinal distraction device according to the invention, the two blades of which are positioned close to each other (FIG. 1) and spaced apart from each other (FIG. 2);

DETAILED DESCRIPTION OF THE INVENTION

Figure 3:
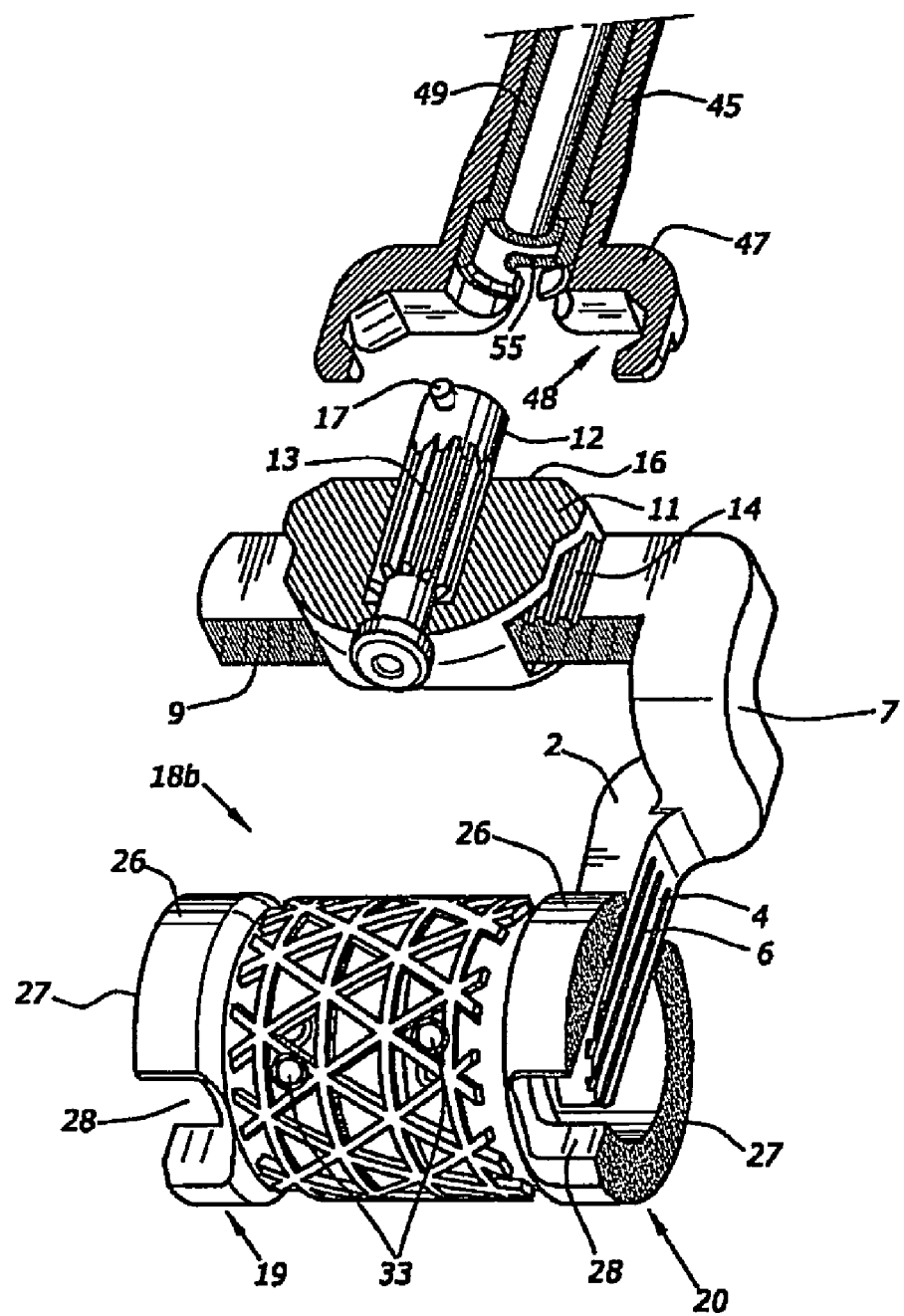
FIG. 3 shows a perspective and partially cutaway view of the preceding distraction device, carrying an example of an implant according to the invention, and also a perspective and partially cutaway view of an example of a tool for rotating the pinion of the distraction device.

The first element of the instrumentation according to the invention is a distraction device or distractor 1.

Its function, after the surgeon has performed a corpectomy of the damaged vertebra 51, is to establish between the vertebral plateaus of two healthy vertebrae 52, 53, situated above and below the damaged vertebra 51, a distance that will permit insertion of the implant 18a, 18b, which will be described further below.

This distractor 1 comprises two blades 2, 3, each of them having a flat outer face 4, 5. These outer faces 4, 5 are the ones intended to come into contact with the vertebral plateaus. They preferably comprise striations 6 for providing gripping contact with the vertebral plateaus, limiting the possibilities of the blades 2, 3 sliding. When the distractor 1 is assembled, they must be maintained substantially parallel to each other (in the example shown). For this purpose, the blades 2, 3 are each connected via a sinuous portion 7, 8 to a rectilinear portion 9, 10. These rectilinear portions are inserted into a central part 11 which keeps them parallel to each other and oriented in the direction in which the blades 2, 3 are to be spaced apart. The central part 11 encloses a pinion 12 whose teeth 13 are in contact with racks 14, 15 formed on the faces of the rectilinear portions 9, 10 directed toward it. One end of the pinion 12 protrudes from the rear face 16 of the central part 11 and is traversed by a pin 17 which allows the surgeon, using a suitable instrument of which an example will be described below, to turn the pinion 12 and thereby move the blades 2, 3 of the distractor 1 toward or away from each other, between a position of minimum spacing "d" (FIG. 1) and a position of maximum spacing "D" (FIG. 2). The blades 2, 3 have a length of 35 mm and a width of 7 mm, for example, so as to be able to extend in length over the greater part of the vertebral plateaus and to present a sufficient area of contact with the vertebral plateaus.

The second element of the instrumentation is an implant 18a, 18b of generally cylindrical shape, for which several types of configuration may be envisioned.

Figure 4A:
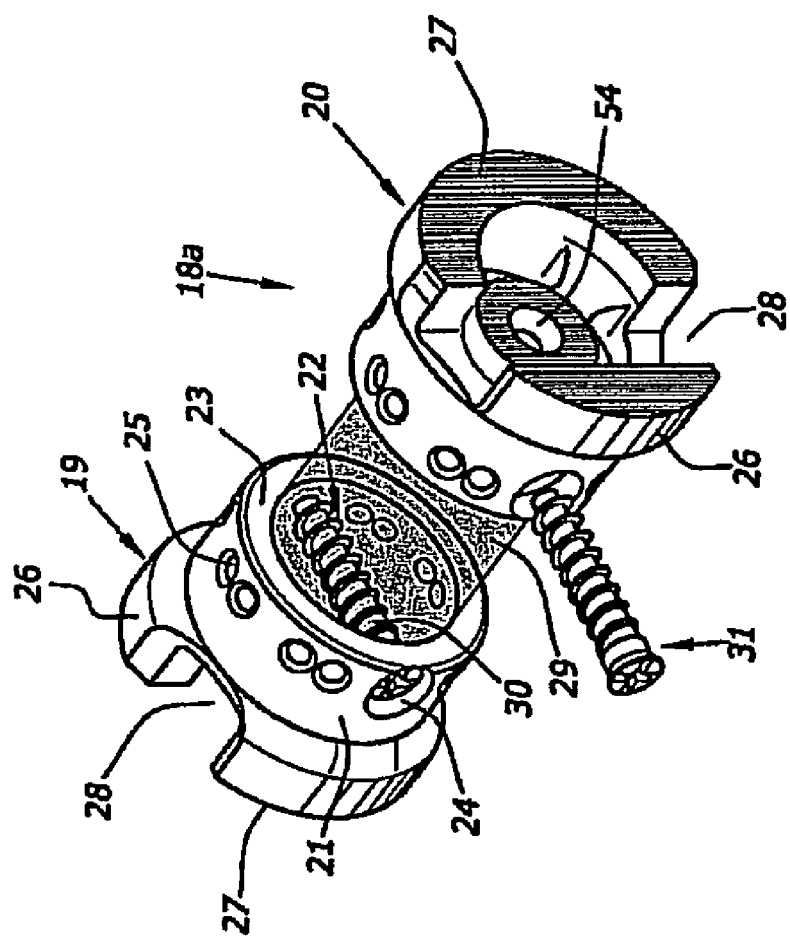
FIG. 4 shows perspective views of two examples (FIGS. 4a and 4b) of implants according to the invention.

In the configuration in FIG. 4a, the implant 18a has two plates 19, 20, of which each comprises:

a cylindrical portion 21 having a longitudinal aperture 22 on its face 23 intended to be directed toward the other plate 19, 20 of the implant 18a, and a series of threaded apertures 24, 25 on its side wall;

an end portion 26 that has a flat outer face 27 intended to come into contact with a vertebral plateau when the implant 18a is fitted in place; this outer face 27 also has a slot 28 whose width corresponds to the width of a blade 2, 3 of the distractor 1 and whose height is slightly greater than that of a blade 2, 3 of the distractor 1.

The implant 18a also has a central part 29, which is substantially cylindrical in the example shown, connects the plates 19, 20 and is formed by a bone graft. The graft is engaged in the longitudinal apertures 22 of the plates 19, 20 and is held there by screws 30, 31 that pass through threaded apertures 24 of large diameter formed on the side walls of the plates 19, 20.

Apertures 54 allow the bone graft to undergo vascularization and to pass through the plates 19, 20 and come into contact with the vertebral plateaus that are to be treated, thereby achieving bone fusion of the two healthy vertebrae 52, 53 enclosing the damaged vertebra 51.

Figure 4B:
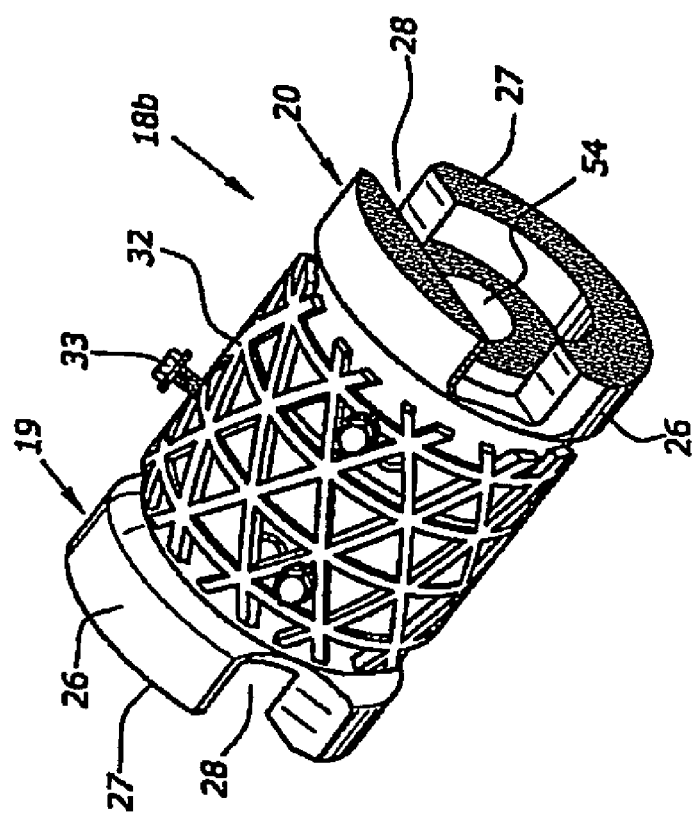

In the configuration in FIG. 4b, the implant 18b is similar to the preceding one, except that the central part connecting the plates 19, 20 is composed of a tubular lattice 32 of titanium (for example) enclosing, if appropriate, a bone graft (not shown). The lattice 32 is fixed to the plates 19, 20 by screws 33 that pass through threaded apertures 25 of small diameter formed on the side walls of the plates 19, 20.

If no bone graft is to be placed in the central part of the implant, the presence of the apertures 54 in the plates 19, is not necessary.

The tubular lattice 32 could be replaced by a tube with a solid wall. However, because of its apertures, the lattice 32 permits vascularization of the graft, if one is present, and circulation of fluid.

It should also be noted that, in a variant not shown here, it is possible for the central part 29 and the plates 19, 20 of the implant 18 to form a single piece.

In the example shown, the plates 19, 20 have the two types of threaded apertures 24, 25 so as to be able to be used either with a graft 29 (FIG. 4a) or a tubular lattice 32 (FIG. 4b) or a tube. Of course, they could have just one type of aperture 24, 25 compatible with one and/or other of these variants of the central part.

For use of the implant 18a, 18b in the thoracolumbar region, the plates 19, 20 have a diameter of the order of 20 mm. The surfaces of their outer faces 27 can be parallel once the implant has been assembled: the vertebral plateaus will then also be parallel when the implant is fitted in place.

The outer faces 27 of the plates 19, 20 are preferably covered with hydroxyapatite or a similar material that stimulates bone growth, in such a way as to ensure better anchoring of the implant 18a, 18b on the vertebral plateaus.

Figure 5:
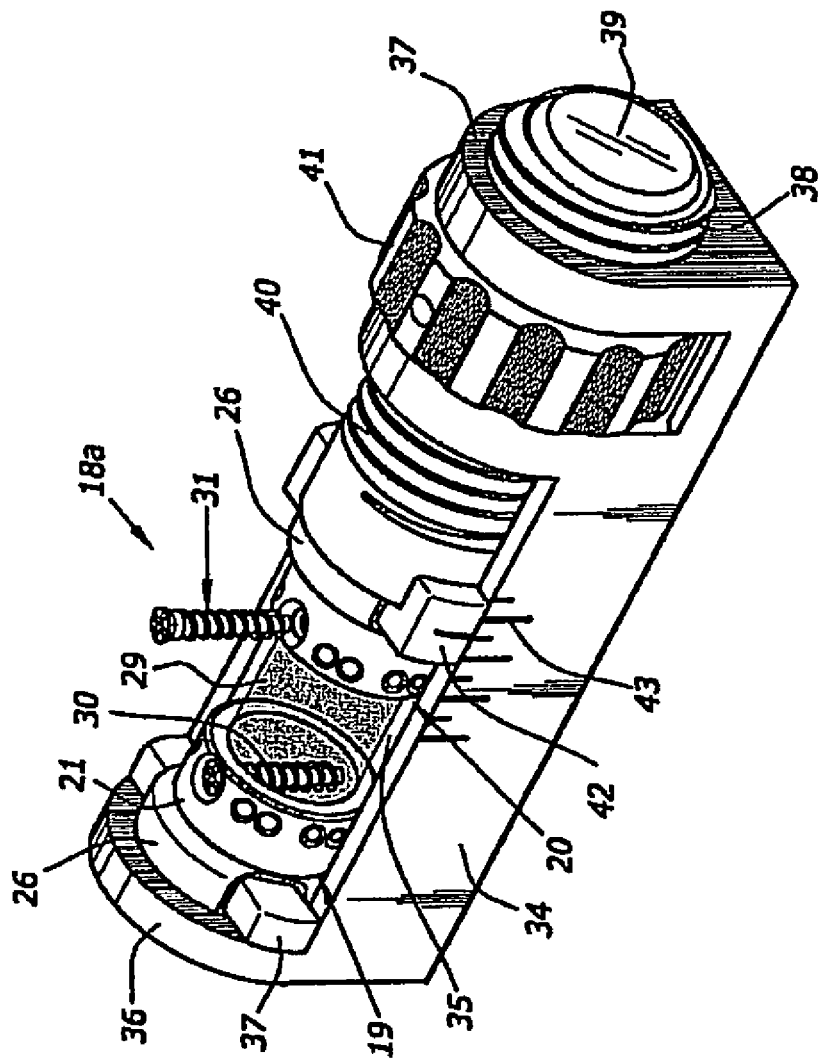
FIG. 5 shows a perspective view of a device for assembling an implant according to the invention.

A device such as the one shown in FIG. 5 can advantageously be used for assembling the implant 18a, 18b.

It is composed of a base 34 that defines a seat 35 in which are placed the different elements of the implant (which, in the example shown, is of the type 18a according to FIG. 4a). The first of the ends of the base is a fixed wall 36 and carries, on its face directed toward the seat 35, a horizontal crosspiece 37 whose width corresponds to that of a slot 28 in a plate 19, 20 of the implant 18a. The second end of the base 34 is a wall 37 with an aperture 38 through which passes a cylindrical rod 39 with an outer thread 40. A threaded knurled wheel 41, held in the base 34 and traversed by the rod 39, allows the user to move the rod 39 back or forward inside the seat 35 of the base 34. At its end directed toward the inside of the base 34, the rod 39 has a horizontal crosspiece 42 which, like the crosspiece 37 at the first end of the base 34, has a width corresponding to that of a slot 28 in a plate 19, 20 of the implant 18a. The two crosspieces 38, 42 are therefore strictly facing each other.

During preparation of the implant 18a, prior to its being implanted, the plates 19, 20 are placed in the seat 35 in such a way as to engage on the crosspieces 37, 42. It is in this way possible to ensure that, after the implant 18a has been assembled, the slots 28 will be strictly parallel. A cylindrical bone graft 29 is then inserted into one of the plates 19, 20 and fixed there with the aid of screws 30, 31, and the two plates 19, 20 are moved together by turning the knurled wheel 41, in such a way as to obtain insertion of the graft 29 in the other of the plates 19, 20. Thereafter, the graft 29 is fixed in the other of the plates 19, 20 by screws 30, 31. By means of graduations 43 marked on the base 34, it is possible to ensure that the total length of the assembled implant 18a is indeed the length desired by the surgeon.

The assembling device in FIG. 5 can of course also be used to assemble an implant 18b whose cylindrical central part is composed of a tube or a tubular mesh 32 enclosing a bone graft.

Figure 6:
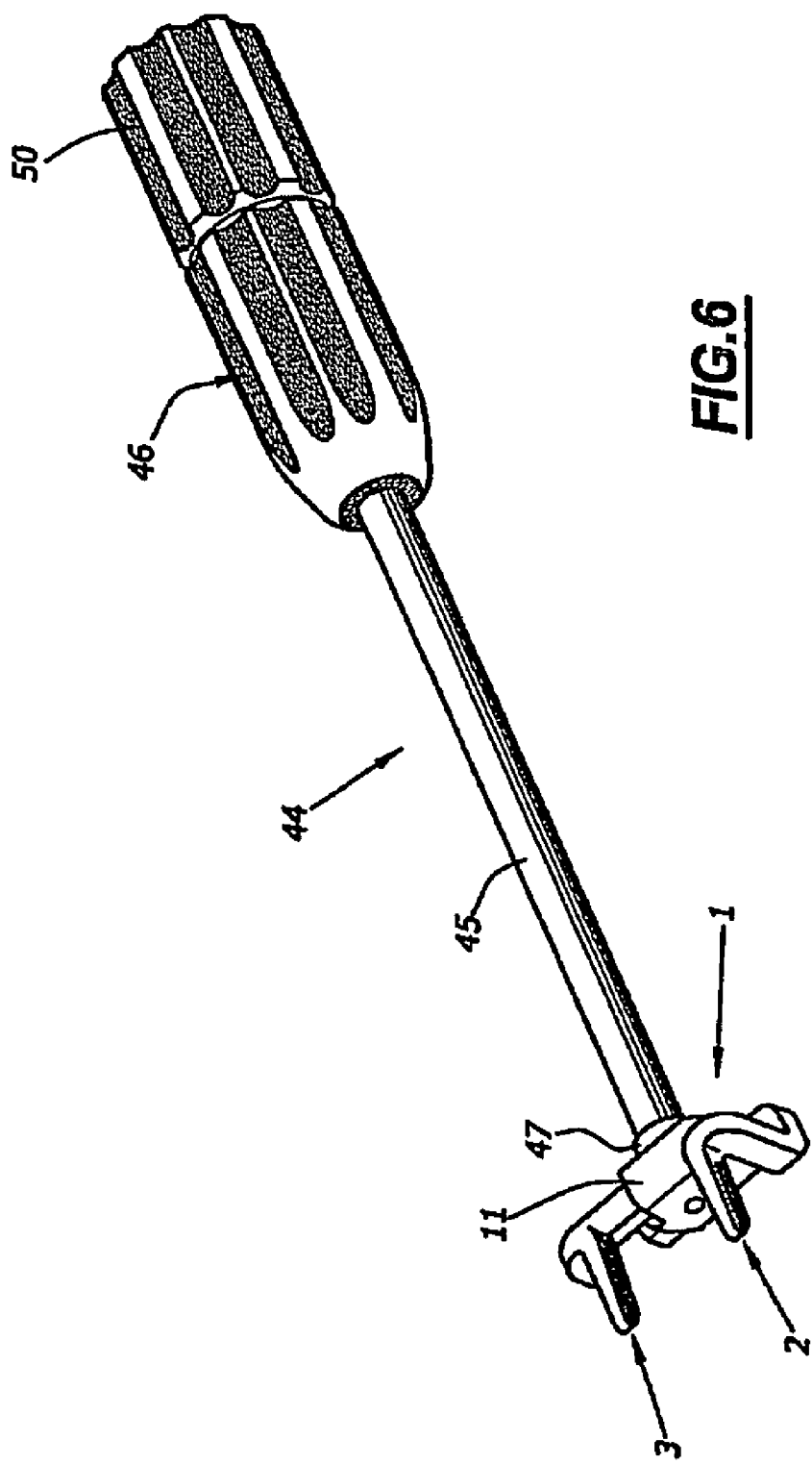
FIG. 6 shows a perspective view of an example of a tool for rotating the pinion of the distraction device, and the distraction device itself.

The instrumentation can be advantageously supplemented by a tool 44, shown in FIG. 6, by means of which the spacing of the blades 2, 3 of the distractor 1 can be regulated. It comprises a rod 45 provided at one of its ends with a handle 46 and at the other of its ends with a bushing 47 whose internal space 48 is designed such that the rod 45 can be engaged, without possible rotation, against the rear face 16 of the central piece 11 of the distracter 1 (see FIG. 3). Inside this rod 45 there is an inner rod 49 that can turn about its longitudinal axis when the surgeon turns a handle 50 placed in continuation of the handle 46 connected to the tube 45.

The end 55 of the inner rod 49 is designed in such a way as to be able to engage with the pin 17 of the pinion 12. When the pin 17 is gripped by the end 55 of the inner rod 49, a rotation of the handle 50 connected to the inner rod 49 is transmitted to the pinion 12, which allows the blades 2, 3 to be moved relative to each other in such a way as to bring them together or space them apart. Blocking means (not shown) of the inner rod 49 allow the spacing between the blades 2, 3 to be maintained at a value chosen by the surgeon.

Figure 7:
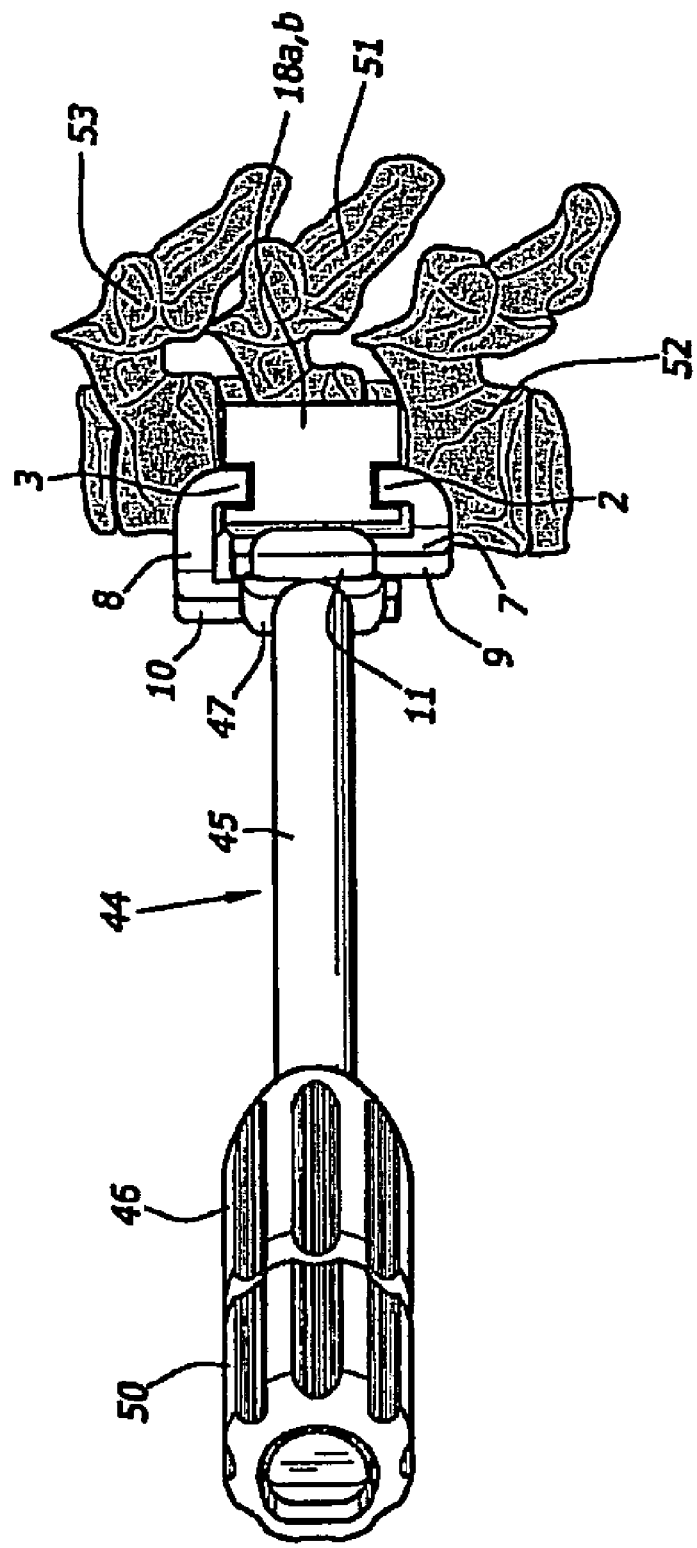
FIG. 7 shows an implant according to the invention during implantation.

The invention is used in the manner set out below and as shown in FIG. 7.

In a first step, the surgeon performs a corpectomy on the damaged vertebra 51, so as to leave only the healthy parts in place and free a space in which the implant 18a, 18b will be able to be inserted.

The surgeon then inserts the blades 2, 3 of the distractor 1 between the vertebral plateaus of the healthy vertebrae 52, 53 surrounding the damaged vertebra 51. Then, with the aid of the tool 44 (or any other instrument with an equivalent function), he gradually increases the spacing between the blades 2, 3 in such a way that the intervertebral space in question undergoes a distraction that is slightly greater than the height of the implant. Once this distraction is obtained, the distractor 1 is blocked.

The surgeon then inserts the implant 18a, 18b, which has been prepared in advance, between the blades 2, 3 of the distractor 1. For this purpose, the slots 28 of the plates 19, 20 permit extremely simple sliding of the implant 18a, 18b between the blades 2, 3. It will also be noted that the configuration of the sinuous portions 7, 8 continuing the blades 2, 3 advantageously allows the space situated to the rear of the blades 2, 3 to be freed in order to permit insertion of the implant 18a, 18b between the blades 2, 3, the central part 11 being offset at an angle (for example about 30°) with respect to this space. In this way, the tool 44 does not interfere with the implant 18a, 18b. FIG. 7 shows this stage of the operation.

The surgeon then actuates the tool 44 in such a way as to reduce the spacing between the blades 2, 3 until the vertebral plateaus of the healthy vertebrae 52, 53 come into contact with the flat outer faces 27 of the plates 19, 20 of the implant 18a, 18b. When this contact is made, the distractor 1 is withdrawn.

Finally, the surgeon can complete the operation by fitting anterior or posterior instrumentation for stabilizing the region of the spine in question. This instrumentation in most cases includes one or more longitudinal rods or plates that are fixed on the healthy vertebrae 52, 53 by bone-anchoring elements (screws or hooks). This instrumentation ensures compression of the implant 18a, 18b.

The different elements of the implant 18a, 18b can be made of any biocompatible material able to withstand the axial loads to which they will be exposed: stainless steel, titanium, carbon fibers, etc. The diameter of the implant 18a, 18b can, for example, be from 16 to 25 mm depending on the region of the spine where it is to be fitted. A diameter of 16 mm is generally suitable for the thoracic region, and a diameter of 25 mm for the lumbar region.

In the variant of the invention shown in the figures, the outer faces 27 of the implant 18a, 18b are parallel. However, it is also possible for them to be made converging at an angle of a few degrees (4° for example), so as to reconstruct a lordosis or kyphosis of the spine after the implant 18a, 18b has been fitted in place. In this case, the configuration of the base 34 of the assembling device must be modified accordingly. It is also possible to provide a distractor 1 whose blades 2, 3 form a corresponding angle. The general cylindrical shape of the implant described and shown here is just one example and is not obligatory. The shape of the assembling device described and shown here can be adapted in an obvious way to that of a non-cylindrical implant.

The means allowing the surgeon to turn the pinion 12 are not limited to the pin 17 that has been described and shown.

For example, they could comprise surfaces formed at the end of the pinion and coming into engagement with a bushing formed at the end of the inner rod 49 of the tool 44 (or another tool with an equivalent function). Moreover, it is possible to have both a pin 17 and surfaces at the same time, in such a way as to allow several designs of tools 44 to be used with one and the same distractor 1.

The invention has the particular advantage of allowing the implant to be implanted by minimally invasive surgery and of permitting excellent stabilization of the spine, especially in cooperation with a customary stabilization device with rod(s) or plate(s).

The invention claimed is:

1. Assembly comprising:
    an implant intended to replace all or part of a vertebral body of a damaged vertebra, having a central part comprising a bone graft and/or a tubular cage with a solid or perforated wall; two plates which are arranged at ends of said central part and having flat outer faces intended to come into contact with a vertebral plateaus of a healthy vertebrae enclosing the damaged vertebra and are each provided with a slot, and
    a spinal distraction device, having: two blades which face each other and each having a flat outer face intended to come into contact with the vertebral plateau of the healthy vertebra, said blades each being connected to a rack via a sinuous portion, said sinuous portion being configured to form an offset between said blades and a central part to permit free access to space posterior to said blades; said central part being traversed by said racks and enclosing a pinion having teeth in contact with said racks in such a way that a rotation of said pinion causes said blades to move toward or away from each other, and means for controlling said pinion in rotation,
    wherein said slots are each designed to receive said blades, a width of these slots corresponding to widths of these blades, but a depth of these slots being greater than or equal to a thickness of said blades.

2. Assembly according to claim 1, wherein the outer faces of the blades are parallel.

3. Assembly according to claim 2, wherein the outer faces of said plates are parallel.

4. Assembly according to claim 1, wherein the outer faces of said blades form an angle corresponding to an angle of lordosis or kyphosis of the spine.

5. Assembly according to claim 4, wherein the outer faces of said plates form an angle corresponding to a lordosis or kyphosis of the spine.

6. Assembly according to claim 1, wherein said plates have apertures.

7. Assembly according to claim 1, wherein said central part and said plates form a single piece.

8. Assembly according to claim 1, wherein said plates are attached and fixed to said central part.

9. Assembly according to claim 8, wherein said plates have threaded holes for engagement of screws for ensuring connection to said central part.

10. Assembly according to claim 1, wherein said control means comprise a tool that is able to cooperate with said pinion in a movable manner.

11. Assembly according to claim 10, further comprising a pin passing through said pinion and permitting engagement of this pinion with said tool.

12. Assembly according to claim 10, further comprising surfaces formed at one end of said pinion and permitting engagement of this pinion with said tool.

13. Device for assembling an implant that forms part of an assembly according to claim 1, further comprising a base provided with a seat, of which an end is a fixed wall which on a face directed toward the seat has a horizontal crosspiece with a width corresponding to that of a slot of the implant, and of which another end is a rod movable along a longitudinal axis of the seat and having, on its face directed toward the seat, a crosspiece with a width corresponding to that of a slot of the implant, said crosspieces facing each other.

14. Tool forming part of an assembly according to claim 1, further comprising a rod provided at one end with a handled and at another end with a bushing whose internal spaced is designed to engage, without possible rotation, with a posterior face of the central part of the distraction device, said rod enclosing an inner rod which can be controlled so as to turn about its longitudinal axis and can be blocked in rotation and, at its end, has means for engaging it with the pinion.

* * * * *